United States Patent [19]

Hallgren

[11] Patent Number: 4,471,132

[45] Date of Patent: Sep. 11, 1984

[54] METHOD FOR MAKING POLYALKOXYAMINOSILANES

[75] Inventor: John E. Hallgren, Scotia, N.Y.

[73] Assignee: General Electric Company, Schenectady, N.Y.

[21] Appl. No.: 499,639

[22] Filed: May 31, 1983

[51] Int. Cl.$^3$ .............................................. C07F 7/10
[52] U.S. Cl. ................................................. 556/410
[58] Field of Search ........................................ 556/410

[56] References Cited

U.S. PATENT DOCUMENTS 4,115,427  9/1978  Kötzsch et al. ................ 556/410 X

FOREIGN PATENT DOCUMENTS 0735595  5/1980  U.S.S.R. .............................. 556/410

*Primary Examiner*—Paul F. Shaver
*Attorney, Agent, or Firm*—William A. Teoli; James C. Davis, Jr.; James Magee, Jr.

[57] ABSTRACT

A method is provided for making polyalkoxyaminosilanes by effecting reaction between polyalkoxysilane and amine in the presence of a transition metal catalyst. The polyalkoxyaminosilanes are intermediates for room temperature vulcanizable silicone compositions.

4 Claims, No Drawings

METHOD FOR MAKING POLYALKOXYAMINOSILANES

CROSS REFERENCE TO RELATED APPLICATIONS

Reference is made to the copending application of Mary Ann White et al, Ser. No. 277,524, filed June 26, 1981 now U.S. Pat. No. 4,395,526, for One Package, Moisture Curable, Room Temperature Vulcanizable Oganopolysiloxane Compositions and Method for Making, and copending application Ser. No. 499,589, May 31,1983, where both applications are assigned to the same assignee as the present invention and incorporated herein by reference.

BACKGROUND OF THE INVENTION

The present invention relates to a method for making polyalkoxyaminosilanes based on the reaction between a polyalkoxysilane having a hydrogen atom attached to silicon and an amine in the presence of a transition metal catalyst.

As shown in copending application Ser. No. 277,524 of Mary Ann White et al, alkoxy silanes having leaving groups such as amino, enoxy, amido, ureido, etc., can be used as scavengers for hydroxy radicals and room temperature vulcanizable organopolysiloxane compositions to impart improved stability over extended shelf periods at ambient temperatures or under accelerated aging conditions at elevated temperatures.

Prior to the present invention N-silylamines were prepared from chlorosilanes in the presence of an excess of an appropriate amine, as shown by R. Fessenden and J. S. Fessenden, Chem. Rev. 61 361 (1961). Alkali metal amides as shown by U. Wannagat, Advanced Inorganic Radio Chemistry, 6 225 (1964), shows the preparation of N-trialkylsilylamines. Alkylaryl-N-silylamines have also been prepared using a palladium or platinum catalyst as shown by W. Fink, Helv. Chim. Acta. 49 1408 (1966).

The present invention is based on my discovery that polyalkoxyaminosilanes of the formula,

can be made by effecting reaction between a polyalkoxysilane of the formula,

and an amine of the formula,

where R is a $C_{(1-8)}$ aliphatic organic radical selected from alkyl radicals, alkylether radicals, alkylester radicals, alkylketone radicals and alkylcyano or a $C_{(7-13)}$ aralkyl radical, $R^1$ is a $C_{(1-13)}$ monovalent substituted or unsubstituted hydrocarbon radical, $R^2$ is selected from hydrogen or a $C_{(1-8)}$ alkyl radical and a has a value of 0 or 1 and b is a whole number equal to 0 to 2 inclusive. Reaction between the polyalkoxysilane and the amine is effected in the presence of a transition metal catalyst such as palladium.

STATEMENT OF THE INVENTION

There is provided by the present invention a method for making a polyalkoxyaminosilane of formula (1) which comprises
(A) effecting reaction between a polyalkoxysilane of formula (2) and an amine of formula (3) in the presence of an effective amount of a transition metal catalyst,
(B) recovering the polyalkoxyamine silane from the mixture of (A).

Radicals included within R of formula (1) are for example, $C_{(1-8)}$ alkyl radicals, for example, methyl, ethyl, vinyl, propyl, butyl, pentyl, etc.; radicals included within $R^1$ are, for example, $C_{(1-8)}$ alkyl radicals, for example, methyl, ethyl, propyl, butyl, pentyl, etc.; alkenyl radicals, such as, vinyl, allyl, etc.; $C_{(6-13)}$ aryl radicals, for example, phenyl, xylyl, tolyl, naphthyl, etc. halogenated derivatives thereof. Radicals included by $R^2$ are, for example, hydrogen and some $R^1$ radicals as previously defined. In instances where R and $R^2$ can be more than one radical, these radicals can be the same or different.

There are included by the polyalkoxysilanes of formula (2), compounds such as
$CH_3Si(OCH_3)_2H$,
$CH_3Si(OC_2H_5)_2H$,
$C_2H_3Si(OCH_3)_2H$,
$C_6H_5Si(OCH_3)_2H$,
$C_6H_5Si(OC_3H_7)_2H$,
$C_6H_{13}Si(OC_2H_5)_2H$,
$C_6H_{13}Si(OCH_3)_2H$,
$C_2H_5Si(OCH_3)_2H$,
$C_2H_5Si(OC_2H_5)_2H$, etc.

There are included by the amines of formula (3) compounds such as ammonia, dimethylamine, methylamine, diethylamine, ethylamine, propylamine, di-n-propylamine and di-iso-propylamine. Other amines such as piperidine, imidazole, etc., also can be used Transition metal catalysts which can be used in the practice of the present invention are, for example, palladium on carbon, nickel on carbon, nickel thiophenoxide, nickel chloride, nickel carbonate, nickel acetate, etc.

In the practice of the invention, reaction is effected between the polyalkoxysilane of formula (1) and the amine of formula (2) in the presence of an effective amount of transition metal catalyst.

There can be utilized from about 0.1 to 10 moles of amine of formula (2) per mole of polyalkoxysilane of formula (1) and preferable 0.9 to 1.1 moles of amine. Reaction can be performed in the presence of an inert organic solvent such as chlorobenzene, toluene, orthodichlorobenzene, octane, etc. An effective amount of transition metal catalyst is 0.01 to 10% by weight of the mixture. Temperatures which can be used are, for example, from 25° C. to 250° C. and preferably 50° C. to 120° C. Preferably the reaction is conducted under autogenous conditions, however, pressures of from 15 to 1000 psi and preferably 30 to 60 psi can be used if desired. If desired, a vapor phase reaction can be carried out where a mixture of the polyalkoxysilane and amine vapor is passed through a bed of transition metal catalyst on an appropriate port.

In order that those skilled in the art will be better able to practice the invention, the following examples are given by way of illustration and not by way of limitation. All parts are by weight.

EXAMPLE 1

A mixture of 5 grams of methyldimethoxysilane, 5 grams of methyl amine, 0.05 gram of 5% palladium on carbon and 0.200 gram of hexane standard was heated in a 21 ml Hastelloy-C pressure reactor to 80° C. for 1 hour and then cooled to −30° C. The reactor was carefully to vent hydrogen gas before it was opened. The mixture was then analyzed by GC. There was obtained 4.2 grams, or a 65% yield of methyldimethoxymethylaminosilane, 0.42 grams of methyltrimethoxysilane and 0.77 gram of methylmethoxybis(methylamino)silane. The reaction products were further identified by their GC-MS and NMR data.

EXAMPLE 2

A mixture of methyldimethoxysilane and methylamine is passed through a bed of palladium on carbon on a support at atmospheric pressure, at a temperature of between room temperature and about 100° C. There is obtained a 65% yield of methyldimethoxymethylaminosilane. The same procedure was repeated, except that in place of the methylamine there is used propylamine and ammonia resulting in the production of methyldimethoxypropylaminosilane and methyldimethoxyaminosilane. The following table shows the yields (wt %) of the various silanes obtained in the vapor phase reaction study, where %I indicates the percent yield of $CH_3Si(OCH_3)_2NHR$:

| R | I | % MeSi(OMe)$_3$ | % MeSi(OMe)NHR)$_2$ |
|---|---|---|---|
| C$_3$H$_7$ | 77 | 12 | 7 |
| CH$_3$ | 65 | 22 | 12 |

| R | I | % MeSi(OMe)$_3$ | % MeSi(OMe)NHR)$_2$ |
|---|---|---|---|
| H | 67 | 12 | — |

The above results show that the method of the present invention can be used to make a variety of methyldimethoxyaminosilanes.

Although the above examples are directed to only a few of the very many variables which can be used in the practice of the method of the present invention, it should be understood that the present invention is directed to the synthesis of a much broader variety of polyalkoxyaminosilanes based on the reaction of polyalkoxysilane and amine in the presence of an effective amount of a transition metal catalyst.

What I claim as new and desire to secure by Letters Patent of the United States is:

1. A method for making a methyldimethoxyaminosilane selected from the class consisting of methyldimethoxyaminosilane, methyldimethoxymethylaminosilane and methyldimethoxypropylaminosilane which comprises effecting reaction between a methyldimethoxysilane and an amine selected from the class consisting of ammonia, methylamine and propylamine, in the presence of an effective amount of a palladium catalyst and thereafter recovering the methyldimethoxymethylaminosilane.

2. A method in accordance with claim 1 which comprises passing a mixture of the methyldimethoxysilane and the amine to a fixed bed of palladium catalyst at a pressure of from about 1–10 atmospheres and at a temperature of about 30° to about 150° C. and thereafter recovering the methyldimethoxyaminosilane.

3. A method in accordance with claim 1, where the polyalkoxysilane is trimethoxysilane.

4. A method in accordance with claim 1, where the polyalkoxysilane is methyldimethoxysilane.

* * * * *